United States Patent [19]
Del Rossi et al.

[11] Patent Number: 5,108,969
[45] Date of Patent: Apr. 28, 1992

[54] LOW ACIDITY CATALYST FOR CONVERSION OF PARAFFINS TO OLEFINS AND/OR AROMATICS

[75] Inventors: Kenneth J. Del Rossi, Mantua; Ralph M. Dessau, Edison, both of N.J.; Albin Huss, Jr., Chadds Ford, Pa.; Garry W. Kirker, Sewell, N.J.; David O. Marler, Deptford, N.J.; Randall D. Partridge, West Trenton, N.J.

[73] Assignee: Mobil Oil Corp., Fairfax, Va.

[21] Appl. No.: 571,470

[22] Filed: Aug. 22, 1990

Related U.S. Application Data

[60] Division of Ser. No. 469,648, Jan. 24, 1990, Pat. No. 5,019,664, which is a continuation-in-part of Ser. No. 254,524, Oct. 6, 1988, Pat. No. 4,954,325, which is a continuation-in-part of Ser. No. 98,176, Sep. 18, 1987, abandoned, which is a continuation-in-part of Ser. No. 890,268, Jul. 29, 1986, abandoned.

[51] Int. Cl.$^5$ .............................................. B01J 29/30
[52] U.S. Cl. ........................................ 502/66; 502/74
[58] Field of Search ..................................... 502/66, 74

[56] References Cited

FOREIGN PATENT DOCUMENTS

| 98040 | 1/1984 | European Pat. Off. | 502/74 |
| 148048 | 7/1985 | European Pat. Off. | 502/74 |
| 937749 | 9/1963 | United Kingdom | 502/74 |
| 1226132 | 3/1971 | United Kingdom | 502/74 |

Primary Examiner—Carl F. Dees
Attorney, Agent, or Firm—Alexander J. McKillop; Charles J. Speciale; Lori F. Cuomo

[57] ABSTRACT

A low acidity Group VIII metal-containing zeolite MCM-22 catalyst, said zeolite exhibiting an Alpha value of not greater than about 150, is provided for conversion of aliphatic $C_2$ to $C_{12}$ hydrocarbon(s) to olefin(s) and/or aromatic(s).

20 Claims, No Drawings

LOW ACIDITY CATALYST FOR CONVERSION OF PARAFFINS TO OLEFINS AND/OR AROMATICS

CROSS-REFERENCE TO RELATED APPLICATIONS

This application is a division of U.S. patent application Ser. No. 469,648, filed Jan. 24, 1990 now U.S. Pat. No. 5,019,664, which is a continuation-in-part of U.S. patent application Ser. No. 254,524, filed Oct. 6, 1988 now U.S. Pat. No. 4,954,325, which is a continuation-in-part of U.S. patent application Ser. No. 98,176, filed Sep. 18, 1987 (now abandoned) which is a continuation-in-part of U.S. patent application Ser. No. 890,268, filed Jul. 29, 1986 (now abandoned).

BACKGROUND OF THE INVENTION

This invention relates to a particular low acidity zeolite catalyst for converting a paraffinic feed, e.g., a naphtha feedstock, to olefins and/or aromatics.

Zeolitic materials, both natural and synthetic, have been demonstrated in the past to have catalytic properties for various types of hydrocarbon conversion. Certain zeolitic materials are ordered, porous crystalline aluminosilicates having a definite crystalline structure as determined by X-ray diffraction, within which there are a large number of smaller cavities which may be interconnected by a number of still smaller channels or pores. These cavities and pores are uniform in size within a specific zeolitic material. Since the dimensions of these pores are such as to accept for adsorption molecules of certain dimensions while rejecting those of larger dimensions, these materials have come to be known as "molecular sieves" and are utilized in a variety of ways to take advantage of these properties. Such molecular sieves, both natural and synthetic, include a wide variety of positive ion-containing crystalline silicates. These silicates can be described as a rigid three-dimensional framework of $SiO_4$ and Periodic Table Group IIIA element oxide, e.g., $AlO_4$, in which the tetrahedra are cross-linked by the sharing of oxygen atoms whereby the ratio of the total Group IIIA element, e.g., aluminum, and silicon atoms to oxygen atoms is 1:2. The electrovalence of the tetrahedra containing the Group IIIA element, e.g., aluminum, is balanced by the inclusion in the crystal of a cation, e.g., an alkali metal or an alkaline earth metal cation. This can be expressed wherein the ratio of the Group IIA element, e.g., aluminum, to the number of various cations, such as Ca/2, Sr/2, Na, K or Li, is equal to unity. One type of cation may be exchanged either entirely or partially with another type of cation utilizing ion exchange techniques in a conventional manner. By means of such cation exchange, it has been possible to vary the properties of a given silicate by suitable selection of the cation. The spaces between the tetrahedra are occupied by molecules of water prior to dehydration.

Prior art techniques have resulted in the formation of a great variety of synthetic zeolites. Many of these zeolites have come to be designated by letter or other convenient symbols, as illustrated by zeolite Z (U.S. Pat. No. 2,882,243); zeolite X (U.S. Pat. No. 2,882,244); zeolite Y (U.S. Pat. No. 3,130,007); zeolite ZK-5 (U.S. Pat. No. 3,247,195); zeolite ZK-4 (U.S. Pat. No. 3,314,752); zeolite ZSM-5 (U.S. Pat. No. 3,702,886); zeolite ZSM-11 (U.S. Pat. No. 3,709,979); zeolite ZSM-12 (U.S. Pat. No. 3,832,449); zeolite ZSM-20 (U.S. Pat. No. 3,972,983); zeolite ZSM-35 (U.S. Pat. No. 4,016,245); and zeolite ZSM-23 (U.S. Pat. No. 4,076,842), merely to name a few.

The $SiO_2/Al_2O_3$ ratio of a given zeolite is often variable. For example, zeolite X can be synthesized with $SiO_2/Al_2O_3$ ratios of from 2 to 3; zeolite Y, from 3 to about 6. In some zeolites, the upper limit of the $SiO_2/Al_2O_3$ ratio is unbounded. ZSM-5 is one such example wherein the SiO ratio is at least 5 and up to the limits of present analytical measurement techniques. U.S. Pat. No. 3,941,871 (Re. 29,948) discloses a porous crystalline silicate made from a reaction mixture containing no deliberately added alumina in the recipe and exhibiting the X-ray diffraction pattern characteristic of ZSM-5. U.S. Pat. Nos. 4,061,724; 4,073,865; and 4,104,294 describe crystalline silicates of varying alumina and metal content.

Catalytic reforming of naphtha feedstocks has long been known in the petroleum industry. Most naphtha feeds contain large amounts of naphthenes and paraffins and consequently have low octane numbers. By means of various hydrocarbon conversion reactions, catalytic reforming has improved the octane number of naphtha feedstocks. Some of the more important conversion reactions that take place during catalytic reforming are dehydrogenation of naphthenes to aromatics, dehydrocyclization of paraffins to naphthenes and aromatics and isomerization of normal paraffins to isoparaffins. A less desirable reaction which also occurs during reforming is the hydrocracking of paraffins, naphthenes and dealkylation of alkylaromatics to gaseous hydrocarbons such as methane and ethane.

The above reforming reactions have previously been catalyzed by catalysts comprising porous supports, such as alumina, which possess dehydrogenation promoting metal components impregnated or admixed therewith. Platinum on alumina and, more recently, multimetallics, including bimetallics, such as platinum and rhenium on alumina, are examples of such catalysts. Representative multimetallic reforming catalysts are described in U.S. Pat. Nos. 2,848,377; 3,415,737; and 3,953,368, among others.

Conventional reforming catalysts, e.g., platinum and rhenium, are disclosed in U.S. Pat. No. 4,141,859 in admixture with a zeolite such as ZSM-5.

A reforming process is disclosed in U.S. Pat. No. 4,325,808 which utilizes as catalyst, a mixture of a noble-metal component, e.g., platinum, on a refractory inorganic oxide such as alumina and a non-noble metal-containing component, e.g., rhenium, on a large pore zeolite such as mordenite which has been disposed within a refractory inorganic oxide such as alumina.

Certain zeolites have also received considerable attention in recent years for their ability to catalyze the conversion of paraffins to aromatics.

According to U.S. Pat. No. 3,755,486, $C_{6-10}$ hydrocarbons undergo dehydrocyclization to benzene and alkylbenzenes in the presence of a Li, Na or K zeolite X or Y or faujasite impregnated with 0.3 to 1.4 percent Pt.

U.S. Pat. No. 3,756,942 describes a process for the conversion of a feed containing liquid paraffins, olefins or naphthenes and mixtures thereof to aromatic compounds employing a porous synthetic synthetic crystalline silicate such as ZSM-5 as catalyst.

U.S. Pat. No. 3,760,024 discloses the aromatization of a feed containing $C_{2-4}$ paraffins and/or olefins in the absence of added hydrogen employing ZSM-5 as catalyst.

According to U.S. Pat. No. 3,855,115, aromatization of hydrocarbons is accomplished employing rhenium-exchanged ZSM-5.

Aliphatic naphthas are upgraded to products of increased aromatics content by the process disclosed in U.S. Pat. No. 3,890,218. The process employs a zeolite catalyst such as ZSM-5 into which one or more metals which increase the aromatization activity of the zeolite, e.g., zinc or cadmium, have been incorporated.

In the process disclosed in U.S. Pat. No. 4,347,394, light straight-run naphthas and similar mixtures are converted to highly aromatic mixtures, principally benzene, employing a Group VIII metal-containing intermediate pore size zeolite, e.g., ZSM-5, which has been rendered substantially free of acidity by treatment with an alkali metal compound, e.g., NaOH.

Gaseous feedstocks containing ethane are converted to a mixture of benzene, toluene and xylene ("BTX") in the process of U.S Pat. No. 4,350,835 utilizing a gallium-containing zeolite such as ZSM-5. A similar catalyst further containing thorium is disclosed in U.S. Pat. No. 4,629,818.

U.S. Pat. No. 4,435,283 describes a method for dehydrocyclizing alkanes employing as catalyst, a Group VIII metal-containing large pore zeolite which further contains an alkaline earth metal, e.g., zeolite X, Y or L containing Pt and barium.

In accordance with the process disclosed in U.S. Pat. No. 4,720,602, $C_2$ to $C_{12}$ aliphatic hydrocarbons are converted to aromatics over a zeolite catalyst, e.g., ZSM-5, which has been activated with zinc.

SUMMARY OF THE INVENTION

In accordance with the present invention, a process is provided for producing one or more olefin and/or aromatic compounds which comprises contacting under suitable conversion conditions a feedstock containing a substantial amount of at least one $C_2$–$C_{12}$ aliphatic hydrocarbon with a conversion catalyst to provide said olefin(s) and/or aromatic compound(s), said catalyst comprising a Group VIII metal species-containing, low acidity synthetic porous crystalline material, or zeolite, characterized by an X-ray diffraction pattern including values substantially as set forth in Table I, infra, and an Alpha Value as defined, infra, of not greater than about 150.

BRIEF DESCRIPTION OF THE DRAWING

The FIGURE is a graphical representation of process performance data relating to the paraffinic hydrocarbon conversion process of this invention.

DESCRIPTION OF SPECIFIC EMBODIMENTS

The entire contents of applications Ser. Nos. 469,648; 254,524; 98,176; and 890,268 are incorporated herein by reference.

The feed stream to the process of this invention contains at least 20%, and more preferably at least 50%, by weight of aliphatic hydrocarbon(s) containing 2 to 12 carbon atoms. The hydrocarbon can be straight chain, open chain or cyclic and can be saturated or unsaturated. Some contemplated hydrocarbons are ethane, propane, propylene, n-butane, n-butenes, isobutane, isobutene, straight chain, branched chain and cyclic pentanes, pentenes, hexanes, hexenes, heptanes, heptenes, octanes, octenes, nonanes, nonenes, decanes, undecanes, decenes, undecenes, dodecanes and dodecenes. A particularly useful hydrocarbon feedstock herein is a raffinate from a hydrocarbon mixture which has had aromatics removed therefrom by a solvent extraction treatment. Examples of such solvent extraction treatments are described on pages 706–709 of the *Kirk-Othmer Encyclopedia of Chemical Technology*, Third Edition, Vol. 9, John Wiley and Sons, (1980). One such hydrocarbon feedstock is a Udex raffinate, a typical composition of which is as follows:

| Component | Wt. Percent |
|---|---|
| $C_5$ | 6.20 |
| $C_5^=$ | 0.19 |
| $C_6$ | 45.80 |
| $C_6^=$ | 8.49 |
| $C_7$ | 27.93 |
| $C_7^=$ | 3.56 |
| $C_8$'s | 1.87 |
| Benzene | 0.39 |
| Toluene | 3.85 |
| EB | 0.34 |
| Xylene | 0.39 |
| $C_9^+$ Aromatics | 1.18 |

The synthetic porous crystalline material employed as catalyst in the process of this invention is referred to herein as "zeolite MCM-22" or simply "MCM-22".

Zeolite MCM-22 has a composition involving the molar relationship:

$$X_2O_3:(n)YO_2,$$

wherein X is a trivalent element, such as aluminum, boron, iron and/or gallium, preferably aluminum, Y is a tetravalent element such as silicon and/or germanium, preferably silicon, and n is at least about 10, usually from about 10 to about 150, more usually from about 10 to about 60, and even more usually from about 20 to about 40. In the as-synthesized form, zeolite MCM-22 has a formula, on an anhydrous basis and in terms of moles of oxides per n moles of $YO_2$, as follows:

$$(0.005-0.1)Na_2O:(1-4)R:X_2O_3:nYO_2$$

wherein R is an organic. The Na and R components are associated with the zeolite as a result of their presence during crystallization, and are easily removed by post-crystallization methods hereinafter more particularly described.

Zeolite MCM-22 is thermally stable and exhibits high surface area greater than 400 $m^2/gm$ as measured by the BET (Bruenauer, Emmet and Teller) test and unusually large sorption capacity when compared to previously described crystal structures having similar X-ray diffraction patterns. In its calcined form, zeolite MCM-22 appears to be made up of a single crystal phase with little or no detectable impurity crystal phases and has an X-ray diffraction pattern including the lines listed in Table I below:

TABLE I

| Interplanar d-Spacing (Å) | Relative Intensity, $I/I_o \times 100$ |
|---|---|
| 30.0 ± 2.2 | W-M |
| 22.1 ± 1.3 | W |
| 12.36 ± 0.4 | M-VS |
| 11.03 ± 0.2 | M-S |
| 8.83 ± 0.14 | M-VS |
| 6.18 ± 0.12 | M-VS |
| 6.00 ± 0.10 | W-M |
| 4.06 ± 0.07 | W-S |
| 3.91 ± 0.07 | M-VS |

TABLE I-continued

| Interplanar d-Spacing (A) | Relative Intensity, I/Io × 100 |
|---|---|
| 3.42 ± 0.06 | VS | and more specifically the lines listed in Table II below:

TABLE II

| Interplanar d-Spacing (A) | Relative Intensity, I/Io × 100 |
|---|---|
| 30.0 ± 2.2 | W-M |
| 22.1 ± 1.3 | W |
| 12.36 ± 0.4 | M-VS |
| 11.03 ± 0.2 | M-S |
| 8.83 ± 0.14 | M-VS |
| 6.86 ± 0.14 | W-M |
| 6.18 ± 0.12 | M-VS |
| 6.00 ± 0.10 | W-M |
| 5.54 ± 0.10 | W-M |
| 4.92 ± 0.09 | W |
| 4.64 ± 0.08 | W |
| 4.41 ± 0.08 | W-M |
| 4.25 ± 0.08 | W |
| 4.10 ± 0.07 | W-S |
| 4.06 ± 0.07 | W-S |
| 3.91 ± 0.07 | M-VS |
| 3.75 ± 0.06 | W-M |
| 3.56 ± 0.06 | W-M |
| 3.42 ± 0.06 | VS |
| 3.30 ± 0.05 | W-M |
| 3.20 ± 0.05 | W-M |
| 3.14 ± 0.05 | W-M |
| 3.07 ± 0.05 | W |
| 2.99 ± 0.05 | W |
| 2.82 ± 0.05 | W |
| 2.78 ± 0.05 | W |
| 2.68 ± 0.05 | W |
| 2.59 ± 0.05 | W |

These values were determined by standard techniques. The radiation was the K-alpha doublet of copper and a diffractometer equipped with a scintillation counter and an associated computer was used. The peak heights, I, and the positions as a function of 2 theta, where theta is the Bragg angle, were determined using algorithms on the computer associated with the diffractometer. From these, the relative intensities, 100 I/$I_o$, where $I_o$ is the intensity of the strongest line or peak, and d (obs.) the interplanar spacing in Angstroms Units (A), corresponding to the recorded lines, were determined. In Tables I and II, the relative intensities are given in terms of the symbols W=weak, M=medium, S=strong and VS=very strong. In terms of intensities, these may be generally designated as follows:

W=0-20
M=20-40
S=40-60
VS=60-100

It should be understood that these X-ray diffraction patterns are characteristic of all species of zeolite MCM-22. The sodium form as well as other cationic forms reveal substantially the same pattern with some minor shifts in interplanar spacing and variation in relative intensity. Other minor variations can occur depending on the Y to X, e.g., silicon to aluminum, mole ratio of the particular sample, as well as its degree of thermal treatment.

Prior to its use as catalyst herein, the MCM-22 crystals should be subjected to thermal treatment to remove part or all of any organic constituent present therein. In addition, the zeolite MCM-22 crystals should be at least partially dehydrated. This can be accomplished by heating the crystals to a temperature in the range of from about 200° C. to about 595° C. in an atmosphere such as air, nitrogen, etc. and at atmospheric, subatmospheric or superatmospheric pressures for between about 30 minutes to about 48 hours. Dehydration can also be performed at room temperature merely by placing the crystalline material in a vacuum, but a longer time is required to obtain a sufficient amount of dehydration.

Zeolite MCM-22 can be prepared from a reaction mixture containing sources of alkali or alkaline earth metal (M), e.g., sodium or potassium, cation, an oxide of trivalent element X, e.g., aluminum, an oxide of tetravalent element Y, e.g., silicon, an organic (R) directing agent, hereinafter more particularly described, and water, said reaction mixture having a composition, in terms of mole ratios of oxides, within the following ranges:

| Reactants | Useful | Preferred |
|---|---|---|
| $YO_2/X_2O_3$ | 10-60 | 10-40 |
| $H_2O/YO_2$ | 5-100 | 10-50 |
| $OH^-/YO_2$ | 0.01-1.0 | 0.1-0.5 |
| $M/YO_2$ | 0.01-2.0 | 0.1-1.0 |
| $R/YO_2$ | 0.05-1.0 | 0.1-0.5 |

In a preferred method of synthesizing zeolite MCM-22, the $YO_2$ reactant contains a substantial amount of solid $YO_2$, e.g., at least about 30 wt. % solid $YO_2$. Where $YO_2$ is silica, the use of a silica source containing at least about 30 wt. % solid silica, e.g., Ultrasil (a precipitated, spray dried silica containing about 90 wt. % silica) or HiSil (a precipitated hydrated $SiO_2$ containing about 87 wt. % silica, about 6 wt. % free $H_2O$ and about 4.5 wt. % bound $H_2O$ of hydration and having a particle size of about 0.02 micron) favors crystal formation from the above mixture and is a distinct improvement over the synthesis method disclosed in U.S. Pat. No. 4,439,409. If another source of oxide of silicon, e.g., Q-Brand (a sodium silicate comprised of about 28.8 wt. % of $SiO_2$, 8.9 wt. % $Na_2O$ and 62.3 wt. % $H_2O$) is used, crystallization may yield little if any MCM-22 crystalline material and impurity phases of other crystal structures, e.g., ZSM-12, may be produced. Preferably, therefore, the $YO_2$, e.g., silica, source contains at least about 30 wt. % solid $YO_2$, e.g., silica, and more preferably at least about 40 wt. % solid $YO_2$, e.g., silica.

Crystallization of the MCM-22 crystalline material can be carried out at either static or stirred conditions in a suitable reactor vessel, such as, e.g., polypropylene jars or teflon lined or stainless steel autoclaves. The total useful range of temperatures for crystallization is from about 80° C. to about 225° C. for a time sufficient for crystallization to occur at the temperature used, e.g., from about 25 hours to about 60 days. Thereafter, the crystals are separated from the liquid and recovered.

The organic directing agent for use in synthesizing zeolite MCM-22 from the above reaction mixture is hexamethyleneimine.

It should be realized that the reaction mixture components can be supplied by more than one source. The reaction mixture can be prepared either batchwise or continuously. Crystal size and crystallization time of the MCM-22 crystalline material will vary with the nature of the reaction mixture employed and the crystallization conditions.

In all cases, synthesis of the MCM-22 crystals is facilitated by the presence of at least about 0.01 percent, preferably about 0.10 percent and still more preferably about 1 percent, seed crystals based on the total weight of the crystalline product formed.

The MCM-22 crystals can be shaped into a wide variety of particle sizes. Generally speaking, the particles can be in the form of a powder, a granule, or a molded product such as an extrudate having a particle size sufficient to pass through a 2 mesh (Tyler) screen and be substantially retained on a 400 mesh (Tyler) screen. In cases where the catalyst is molded, such as by extrusion, the crystals can be extruded before drying or partially dried and then extruded.

A critical requirement of the low acidity MCM-22 zeolite herein is that it (exclusive of its Group VIII metal component) exhibit an "Alpha Value", or "Alpha Number", not exceeding a certain maximum value. The Alpha Value of the MCM-22 zeolite herein is characteristic of a zeolite possessing a low or limited catalytic cracking activity compared to that of a standard, or reference, cracking catalyst. Alpha Value expresses the relative rate constant (rate of normal hexane conversion per volume of catalyst per unit time) and is related to the activity of silica alumina cracking catalyst taken as having an Alpha Value of 1 (rate Constant=0.016 sec$^{-1}$). Alpha Value can be regarded as a function of zeolite activity, the low Alpha Value of the MCM-22 zeolite herein being indicative of a zeolite possessing relatively little acidity or acid functionality. The test for measuring Alpha Value which was used herein is described in *J. Catalysis*, 61, pp. 390–396 (1980), the contents of which are incorporated by reference herein. In these tests, a constant temperature of 538° C. and variable flow rate were maintained as described in detail in *J. Catalysis*, 61, p. 395.

The Alpha Value of the MCM-22 zeolite employed in the paraffin-to-aromatics conversion of this invention should not exceed about 150. Preferably, the Alpha Value of the zeolite does not exceed 50 and more preferably yet, does not exceed about 10. In possessing some acidity, however, the low acidity MCM-22 zeolite herein is to be regarded as materially different from an essentially non-acidic zeolite, the catalytic properties of which differ significantly from those of low acidity MCM-22 zeolite for the conversion of paraffins to olefins and/or aromatics.

Zeolite MCM-22 of such low Alpha Value can be prepared by a variety of techniques including (a) synthesizing the zeolite with a high silica/alumina ratio, (b) steaming, (c) steaming followed by dealumination and (d) substituting framework aluminum with other trivalent metal species, for example, boron. In the case of steaming, the zeolite can be exposed to steam at elevated temperatures ranging from about 500° F. to about 1200° F. and preferably from about 750° to about 1000° F. This treatment can be accomplished in an atmosphere of 100% steam or an atmosphere consisting of steam and a gas which is substantially inert to the zeolite. A similar treatment can be accomplished at lower temperatures employing elevated pressure, e.g., at from about 350° to about 700° F. with from about 10 to about 200 atmospheres. Specific details of several steaming procedures can be gained from the disclosures of U.S. Pat. Nos. 4,325,994; 4,374,296; and, 4,418,235, the contents of which are incorporated by reference herein. Aside from, or in addition to any of the foregoing procedures, the acidity of MCM-22 zeolite can be reduced by treatment with a base material, e.g., a hydroxide or basic salt of an alkali metal or alkaline earth metal such as sodium hydroxide, sodium carbonate, sodium bicarbonate, sodium nitrate, potassium hydroxide, potassium carbonate, calcium hydroxide, calcium carbonate, barium hydroxide, barium carbonate, etc. If the crystals of MCM-22 zeolite are already substantially free of alkali metal or alkaline earth metal, alkali metal and/or alkaline earth metal ions can be ion-exchanged into the zeolite to reduce its acidity and thus reduce its Alpha Value to within an acceptable level as required herein.

The low acidity MCM-22 zeolite herein must be associated with at least one Group VIII metal component prior to being used in the paraffin conversion process of this invention. The expression "Group VIII metal species" as used herein contemplates the metal per se or a compound thereof. The Group VIII noble metals and their compounds, e.g., platinum, palladium, iridium, rhenium and rhodium, or combinations thereof can be used. The preferred metals are platinum and palladium and of these, platinum is the most preferred. The Group VIII metal component can be physically and/or chemically associated with the zeolite and/or any binder or matrix material with which the zeolite may be composited. For example, the Group VIII metal species can be impregnated into the MCM-22 crystals after they are formed or the metal can be included in the reaction mixture from which this zeolite is formed. The Group VIII metal can also be impregnated in, or on, the zeolite such as, for example, by, in the case of platinum, treating the zeolite with a solution containing a platinum metal-containing ion. Thus, suitable platinum compounds for this purpose include chloroplatinic acid, platinous chloride and any of various compounds containing a platinum amine complex. The amount of Group VIII metal present in the MCM-22 can vary from about 0.01 to 5.0 weight percent, preferably about 0.1 to about 2.0 weight percent, and most preferably about 0.2 to about 1.0 weight percent.

In order to further enhance the selectivity of the low acidity, Group VIII metal species-containing MCM-22 catalyst of this invention, the catalyst can be further associated with one or more species of elements such as tin, indium, thallium, lead and/or sulfur. Known and conventional techniques, e.g., those described above, can be employed in providing the zeolite catalyst herein with these elements which can be present at levels similar to those indicated above for the Group VIII metal component.

It can be advantageous to incorporate the crystals of zeolite MCM-22 into some other materials, i.e., a matrix or binder, which is resistant to the temperature and other conditions employed in the conversion of paraffin to aromatics as provided by this invention. Useful matrix materials include both synthetic and naturally-occurring substances, e.g., inorganic materials such as clay, silica and/or metal oxides. Such materials can be either naturally-occurring or can be obtained as gelatinous precipitates or gels including mixtures of silica and metal oxides. Naturally-occurring clays which can be composited with MCM-22 include those of the montmorillonite and kaolin families, which families include the sub-bentonites and the kaolines commonly known as Dixie, McNamee-Georgia and Florida clays or others in which the main mineral constituent is haloysite, kaolinite, dickite, nacrite or anauxite. Such clays can be used in the raw state as originally mined or initially subjected to calcination, acid treatment or chemical modification.

In addition to the foregoing materials, the zeolite catalyst can be composited with a porous metal oxide binder material such as alumina, titania, zirconia, silica, silica-alumina, silica-magnesia, silica-zirconia, silica-thoria, silica-beryllia, silica-titania, etc., as well as ternary oxides compositions such as silica-alumina-thoria, silica-alumina-zirconia, silica-alumina-magnesia, silica-magnesia-zirconia, etc. The binder material can be in the form of a cogel.

In some cases, it may be advantageous to employ as the binder material, one or more oxides of metals of Groups IVA and/or IVB of the Periodic Table of the Elements. These oxides possess no, or relatively little, acidity. Particularly useful oxides of this kind are those of silicon, germanium, titanium and zirconium. In this embodiment, combinations of such low or non-acidic oxides with other oxides including relatively acidic oxides such as alumina are also useful provided that at least about 40 weight percent, and preferably at least 50 weight percent, of the total metal oxide binder is one or a combination of the aforesaid Group IVA and/or Group IVB metal oxides. Thus, mixtures of oxides which can be used to provide the binder material herein include titania-alumina, titania-magnesia, titania-zirconia, titania-thoria, titania-beryllia, titania-silica-thoria, silica-alumina-zirconia, silica-alumina, magnesia, silica-titania-zirconia, and the like. It may be further advantageous to provide at least part of the Group IVA and/or IVB metal oxide binder, e.g., an amount representing from 1 to 100 weight percent and preferably from about 2 to about 60 weight percent of the total binder material, in colloidal form so as to facilitate the extrusion of the zeolite bound therewith.

The conversion of paraffin to aromatic hydrocarbon in accordance with the process of this invention is conducted so that a feed containing a relatively high percentage, e.g., at least 20 wt. %, preferably at least 50 wt. %, of $C_2$–$C_{12}$ aliphatic hydrocarbon(s) is contacted with the low acidity Group VIII metal-containing zeolite MCM-22 herein in a reaction zone such as, for example, a fixed or fluid bed of the catalyst composition under effective conversion conditions. In a typical embodiment of the process of this invention, the feed stream is introduced into the reaction zone at a temperature within the range of from about 600° F. to about 1400° F. preferably from about 800° F. to 1000° F., a pressure within the range of from about atmospheric to about 400 psig, preferably from about 50 to about 250 psig, and a liquid hourly space velocity (LHSV) of from about 0.1 hr$^{-1}$ to about 100 hr$^{-1}$, preferably from about 0.5 hr$^{-1}$ to 5 hr$^{-1}$.

In order to more fully illustrate the process of this invention and the manner of practicing same, the following examples are presented. In examples illustrative of the synthesis of zeolite MCM-22, whenever sorption data are set forth for comparison of sorptive capacities for water, cyclohexane and/or n-hexane, they were Equilibrium Adsorption values determined as follows:

A weighed sample of the calcined adsorbent was contacted with the desired pure adsorbate vapor in an adsorption chamber, evacuated to less than 1 mm Hg and contacted with 12 Torr of water vapor or 40 Torr of n-hexane or 40 Torr of cyclohexane vapor, pressures less than the vapor-liquid equilibrium pressure of the respective adsorbate at 90° C. The pressure was kept constant (within about ±0.5 mm Hg) by addition of adsorbate vapor controlled by a manostat during the adsorption period, which did not exceed about 8 hours. As adsorbate was adsorbed by the MCM-22 crystalline material, the decrease in pressure caused the manostat to open a valve which admitted more adsorbate vapor to the chamber to restore the above control pressures. Sorption was complete when the pressure change was not sufficient to activate the manostat. The increase in weight was calculated as the adsorption capacity of the sample in g/100 g of calcined adsorbant. Zeolite MCM-22 always exhibits Equilibrium Adsorption values of greater than about 10 wt. % for water vapor, greater than about 4.5 wt. %, usually greater than about 7 wt. % for cyclohexane vapor and greater than about 10 wt. % for n-hexane vapor. These vapor sorption capacities are a notable distinguishing feature of zeolite MCM-22.

EXAMPLE 1

One part of sodium aluminate (43.5% $Al_2O_3$, 32.2% $Na_2O$, 25.6% $H_2O$) was dissolved in a solution containing 1 part of 50% NaOH solution and 103.13 parts $H_2O$. To this was added 4.50 parts hexamethyleneimine. The resulting solution was added to 8.55 parts of Ultrasil, a precipitated, spray-dried silica (about 90% $SiO_2$).

The reaction mixture had the following composition, in mole ratios:

| | | |
|---|---|---|
| $SiO_2/Al_2O_3$ | = | 30.0 |
| $OH^-/SiO_2$ | = | 0.18 |
| $H_2O/SiO_2$ | = | 44.9 |
| $Na/SiO_2$ | = | 0.18 |
| $R/SiO_2$ | = | 0.35 | where R is hexamethyleneimine.

The mixture was crystallized in a stainless steel reactor, with stirring, at 150° C. for 7 days. The crystalline product was filtered, washed with water and dried at 120° C. After a 20 hour calcination at 538° C., the X-ray diffraction pattern contained the major lines listed in Table III. The sorption capacities of the calcined material were measured to be:

| | |
|---|---|
| $H_2O$ | 15.2 wt. % |
| Cyclohexane | 14.6 wt. % |
| n-Hexane | 16.7 wt. % |

The surface area of the calcined crystalline material was measured to be 494 m$^2$/g.

The chemical composition of the uncalcined material was determined to be as follows:

| Component | wt. % |
|---|---|
| $SiO_2$ | 66.9 |
| $Al_2O_3$ | 5.40 |
| Na | 0.03 |
| N | 2.27 |
| Ash | 76.3 |
| $SiO_2/Al_2O_3$, mole ratio | 21.1 |

TABLE III

| Degrees 2-Theta | Interplanar d-Spacing (A) | I/Io |
|---|---|---|
| 2.80 | 31.55 | 25 |
| 4.02 | 21.98 | 10 |
| 7.10 | 12.45 | 96 |
| 7.95 | 11.12 | 47 |
| 10.00 | 8.85 | 51 |
| 12.90 | 6.86 | 11 |
| 14.34 | 6.18 | 42 |
| 14.72 | 6.02 | 15 |
| 15.90 | 5.57 | 20 |
| 17.81 | 4.98 | 5 |
| 20.20 | 4.40 | 20 |

TABLE III-continued

| Degrees 2-Theta | Interplanar d-Spacing (A) | I/Io |
|---|---|---|
| 20.91 | 4.25 | 5 |
| 21.59 | 4.12 | 20 |
| 21.92 | 4.06 | 13 |
| 22.67 | 3.92 | 30 |
| 23.70 | 3.75 | 13 |
| 24.97 | 3.57 | 15 |
| 25.01 | 3.56 | 20 |
| 26.00 | 3.43 | 100 |
| 26.69 | 3.31 | 14 |
| 27.75 | 3.21 | 15 |
| 28.52 | 3.13 | 10 |
| 29.01 | 3.08 | 5 |
| 29.71 | 3.01 | 5 |
| 31.61 | 2.830 | 5 |
| 32.21 | 2.779 | 5 |
| 33.35 | 2.687 | 5 |
| 34.61 | 2.592 | 5 |

EXAMPLE 2

A portion of the calcined crystalline product of Example 1 was tested in the Alpha Test and was found to have an Alpha Value of 224.

EXAMPLES 3-5

Three separate synthesis reaction mixtures were prepared with compositions indicated in Table IV. The mixtures were prepared with sodium aluminate, sodium hydroxide, Ultrasil, hexamethyleneimine (R) and water. The mixtures were maintained at 150° C., 143° C. and 150° C., respectively for 7, 8 and 6 days respectively in stainless steel autoclaves at autogenous pressure. Solids were separated from any unreacted components by filtration and then water washed, followed by drying at 120° C. The product crystals were analyzed by X-ray diffraction. Sorption, surface area and chemical analyses results are presented in Table IV. The sorption and surface area measurements were of the calcined product.

TABLE IV

| | Example | | |
|---|---|---|---|
| | 3 | 4 | 5 |
| Synthesis Mixture, mole ratios | | | |
| $SiO_2/Al_2O_3$ | 30.0 | 30.0 | 30.0 |
| $OH^-/SiO_2$ | 0.18 | 0.18 | 0.18 |
| $H_2O/SiO_2$ | 19.4 | 19.4 | 44.9 |
| $Na/SiO_2$ | 0.18 | 0.18 | 0.18 |
| $R/SiO_2$ | 0.35 | 0.35 | 0.35 |
| Product Composition, Wt. % | | | |
| $SiO_2$ | 64.3 | 68.5 | 74.5 |
| $Al_2O_3$ | 4.85 | 5.58 | 4.87 |
| Na | 0.08 | 0.05 | 0.01 |
| N | 2.40 | 2.33 | 2.12 |
| Ash | 77.1 | 77.3 | 78.2 |
| $SiO_2/Al_2O_3$, mole ratio | 22.5 | 20.9 | 26.0 |
| Adsorption, Wt. % | | | |
| $H_2O$ | 14.9 | 13.6 | 14.6 |
| Cyclohexane | 12.5 | 12.2 | 13.6 |
| n-Hexane | 14.6 | 16.2 | 19.0 |
| Surface Area, $m^2/g$ | 481 | 492 | 487 |

EXAMPLE 6

Quantities of the calcined (538° C. for 3 hours) crystalline silicate products of Examples 3, 4 and 5 were tested in the Alpha Test and found to have Alpha Values of 227, 180 and 187, respectively.

EXAMPLE 7

To demonstrate a further preparation of the present zeolite, 4.49 parts of hexamethyleneimine was added to a solution containing 1 part of sodium aluminate, 1 part of 50% NaOH solution and 44.19 parts of $H_2O$. To the combined solution were added 8.54 parts of Ultrasil silica. The mixture was crystallized with agitation at 145° C. for 59 hours and the resultant product was water washed and dried at 120° C.

Product chemical composition (uncalcined), surface area and adsorption analyses results are set forth in Table V:

TABLE V

| Product Composition | |
|---|---|
| C | 12.1 wt. % |
| N | 1.98 wt. % |
| Na | 640 ppm |
| $Al_2O_3$ | 5.0 wt. % |
| $SiO_2$ | 74.9 wt. % |
| $SiO_2/Al_2O_3$, mole ratio | 25.4 |
| Adsorption, wt. % | |
| Cyclohexane | 9.1 |
| N-Hexane | 14.9 |
| $H_2O$ | 16.8 |
| Surface Area, $m^2/g$ | 479 |

EXAMPLE 8

Twenty-five grams of solid crystal product from Example 7 were calcined in a flowing nitrogen atmospheres at 538° C. for 5 hours, followed by purging with 5% oxygen gas (balance $N_2$) for another 16 hours at 538° C.

Individual 3 g samples of the calcined material were ion-exchanged with 100 ml of 0.1N TEABr, TPABr and $LaCl_3$ solution separately. Each exchange was carried out at ambient temperature for 24 hours and repeated three times. The exchanged samples were collected by filtration, water-washed to be halide-free and dried. The compositions of the exchanged samples are tabulated below demonstrating the exchange capacity of the present crystalline silicate for different ions.

| | Exchange Ions | | |
|---|---|---|---|
| Ionic Composition, wt. % | TEA | TPA | La |
| Na | 0.095 | 0.089 | 0.063 |
| N | 0.30 | 0.38 | 0.03 |
| C | 2.89 | 3.63 | — |
| La | — | — | 1.04 |

EXAMPLE 9

The La-exchanged sample from Example 8 was sized to 14 to 25 mesh and then calcined in air at 538° C. for 3 hours. The calcined material had an Alpha Value of 173.

EXAMPLE 10

The calcined sample La-exchanged material from Example 9 was severely steamed at 649° C. in 100% steam for 2 hours. The steamed sample had an Alpha Value of 22, demonstrating that the zeolite had very good stability under severe hydrothermal treatment.

EXAMPLE 11

This example illustrates the preparation of the present zeolite where X in the general formula, supra, is boron. Boric acid, 2.59 parts, was added to a solution containing 1 part of 45% KOH solution and 42.96 parts $H_2O$. To this was added 8.56 parts of Ultrasil silica, and the mixture was thoroughly homogenized. A 3.88 parts quantity of hexamethyleneimine was added to the mixture.

The reaction mixture had the following composition in mole ratios:

| | | |
|---|---|---|
| $SiO_2/B_2O_3$ | = | 6.1 |
| $OH^-/SiO_2$ | = | 0.06 |
| $H_2O/SiO_2$ | = | 19.0 |
| $K/SiO_2$ | = | 0.06 |
| $R/SiO_2$ | = | 0.30 | where R is hexamethyleneimine.

The mixture was crystallized in a stainless steel reactor, with agitation, at 150° C. for 8 days. The crystalline product was filtered, washed with water and dried at 120° C. A portion of the product was calcined for 6 hours at 540° C. and found to have the following sorption capacities:

| | |
|---|---|
| $H_2O$ (12 Torr) | 11.7 wt. % |
| Cyclohexane (40 Torr) | 7.5 wt. % |
| n-Hexane (40 Torr) | 11.4 wt. % |

The surface area of the calcined crystalline material was measured (BET) to be 405 m²/g.

The chemical composition of the uncalcined material was determined to be as follows:

| | |
|---|---|
| N | 1.94 wt. % |
| Na | 175 ppm |
| K | 0.60 wt. % |
| Boron | 1.04 wt. % |
| $Al_2O_3$ | 920 ppm |
| $SiO_2$ | 75.9 wt. % |
| Ash | 74.11 wt. % |
| $SiO_2/Al_2O_3$, molar ratio | = 1406 |
| $SiO_2/(Al + B)_2O_3$, molar ratio | = 25.8 |

EXAMPLE 12

A portion of the calcined crystalline product of Example 11 was treated with $NH_4Cl$ and again calcined. The final crystalline product was tested in the Alpha Test and found to have an Alpha Value of 1.

EXAMPLE 13

This example illustrates another preparation of the zeolite in which X of the general formula, supra, is boron. Boric acid, 2.23 parts, was added to a solution of 1 part of 50% NaOH solution and 73.89 parts $H_2O$. To this solution was added 15.29 parts of HiSil silica followed by 6.69 parts of hexamethyleneimine. The reaction mixture had the following composition in mole ratios:

| | | |
|---|---|---|
| $SiO_2/B_2O_3$ | = | 12.3 |
| $OH^-/SiO_2$ | = | 0.056 |
| $H_2O/SiO_2$ | = | 18.6 |
| $K/SiO_2$ | = | 0.056 |
| $R/SiO_2$ | = | 0.30 | where R is hexamethyleneimine.

The mixture was crystallized in a stainless steel reactor, with agitation, at 300° C. for 9 days. The crystalline product was filtered, washed with water and dried at 120° C. The sorption capacities of the calcined material (6 hours at 540° C.) were measured:

| | |
|---|---|
| $H_2O$ | 14.4 wt. % |
| Cyclohexane | 4.6 wt. % |
| n-Hexane | 14.0 wt. % |

The surface area of the calcined crystalline material was measured to be 438 m²g.

The chemical composition of the uncalcined material was determined to be as follows:

| Component | Wt. % |
|---|---|
| N | 2.48 |
| Na | 0.06 |
| Boron | 0.83 |
| $Al_2O_3$ | 0.50 |
| $SiO_2$ | 73.4 |
| $SiO_2/Al_2O_3$, molar ratio | = 249 |
| $SiO_2/(Al + B)_2O_3$, molar ratio | = 28.2 |

EXAMPLE 14

A portion of the calcined crystalline product of Example 13 was tested in the Alpha Test and found to have an Alpha Value of 5.

EXAMPLE 15

In another illustration of crystalline MCM-22 synthesis, 4.49 parts quantity of hexamethyleneimine was added to a mixture containing 1.00 part sodium aluminate, 1.00 part 50% NaOH, 8.54 parts Ultrasil VN3 and 44.19 parts deionized $H_2O$. The reaction mixture was heated to 143° C. (290° F.) and stirred in an autoclave at that temperature for crystallization. After full crystallinity was achieved, the majority of the hexamethyleneimine was removed from the autoclave by controlled distillation and the zeolite crystals separated from the remaining liquid by filtration, washed with deionized $H_2O$ and dried. The product zeolite was then calcined in nitrogen at 540° C., exchanged with aqueous ammonium nitrate and calcined in air at 540° C. The zeolite was tabletted, crushed and sized to 30/40 mesh. It has the following properties:

| | |
|---|---|
| Surface Area (BET), m²/g | 503 |
| $SiO_2/Al_2O_3$ (molar) | 27 |
| Na, ppm | 495 |
| Alpha | 693 |
| Sorption Properties, wt. % | |
| $H_2O$ | 15.0 |
| $CyC_6$ | 12.5 |
| $n-C_6$ | 16.0 |
| Ash at 1000° C., wt. % | 99.05 |

EXAMPLE 16

This example illustrates the preparation of a low acidity catalyst and its use in the conversion of paraffins.

Ten grams of the zeolite produced in Example 15 were slurried in 100 ml water and to the resultant slurry were added 75 ml of 0.5M NaHCO₃ followed by 50 ml water containing 200 mg Pt(NH₃)₄Cl₂. This mixture was stirred overnight at ambient temperature at a pH of 8.8. The sodium and platinum-exchanged zeolite was filtered, washed, dried and calcined in oxygen by heating to 360° C. at a rate of 0.5° C. per minute and maintained at the final temperature for 1 hour. The low acidity calcined zeolite contained 1.5% Pt, 1.6% Na and 2.4% Al. The pH of the catalyst measured upon a slurry of 0.1 gm of the catalyst in 10 ml of distilled, deionized water was 7.0–7.1.

In a first run employing the catalyst of this example, n-hexane was converted at 538° C., 100 kPa (atmospheric pressure) and a 6:1 mole ratio of hydrogen to n-hexane to provide benzene with a selectivity of 11% at 55–60% conversion.

In a second run employing the catalyst, n-heptane was converted at 482° C., 790 kPa (100 psig) and a 5:1:1 mole ratio of N₂:H₂:C₇. Yields were 29% C₃ and 36% C₄ aliphatics and 4% benzene/toluene/xylene aromatics at 98.8% n-heptane conversion.

EXAMPLE 17

This example illustrates the preparation of a low acidity catalyst for use in the paraffin conversion illustrated in Example 18, infra.

The zeolite produced in Example 15 was subjected to repeated aqueous sodium nitrate exchange/540° C. (1000° F.) air calcination to prepare a low acidity catalyst having an Alpha Value of 2. This sodium form of the zeolite was then exchanged over 4 hours at ambient temperature with 2.6×10⁻³M solution of Pt(NH₃)₄Cl₂ at a pH of 9 followed by washing with deionized water until the zeolite was free of chloride ion and drying thereafter. The zeolite contained 1.0 wt. % Pt. The platinum-loaded zeolite was then calcined in air, the temperature being increased at the rate of 1° C. (2° F.) per minute to a final temperature of 350° C. (660° F.), the zeolite being held at this temperature for 3 hours. Following a twice repeated exchange of the Pt/Na/-zeolite with aqueous sodium nitrate and washing with deionized water, the catalyst was dried at 121° C. (250° F.).

EXAMPLE 18

This example compares the catalytic performance of the low acidity Pt/Na/zeolite catalyst composition of Example 17 with that of a commercial reforming catalyst, namely, Pt/Re/Al₂O₃ (containing 0.22 wt. % Pt and 0.44 wt. % Re).

In each run, 10 cc (approximately 4 grams) of each of the aforesaid catalysts were employed. The catalyst bed was heated at a rate of 104° C./hr (220° F./hr) in 100 cc/min of flowing hydrogen to 510° C. (950° F.) and then held at this temperature for one hour. Conversion data for each catalyst were obtained at process conditions of 510° C. (950° F.), 790 kPa (100 psig), 3:1 H₂/HC mole rate and 3 WHSV with a 100% n-hexane feed.

The results of each run are set forth in Tables VI and VII below and are graphically compared in the FIGURE.

TABLE VI

Dehydrocyclization of n-Hexane Using Catalyst of Invention

| | Hours on Stream | | | | |
|---|---|---|---|---|---|
| | 1 | 5 | 10 | 20 | 24 |
| C₅−, wt. % | | 71.6 | 68.5 | 64.8 | 62.6 |
| Benzene | 33.4 | 20.5 | 18.5 | 18.3 | 17.7 |
| C₇+ Aromatics | 2.3 | 1.7 | 1.5 | 1.3 | 1.3 |
| Total Aromatics | 35.7 | 22.2 | 20.0 | 19.6 | 19.0 |

TABLE VII

Dehydrocyclization of n-Hexane Employing Pt/Re/Al₂O₃ Catalyst

| | Hours on Stream | | |
|---|---|---|---|
| | 3 | 28 | 44 |
| C₅−, wt. % | 49.6 | 41.5 | 36.0 |
| Benzene | 9.2 | 5.8 | 4.3 |
| C₇+ Aromatics | 4.3 | 4.2 | 3.9 |
| Total Aromatics | 13.5 | 10.0 | 8.2 |

As these data show, aromatics production with the low acidity Pt/Na/zeolite catalyst of the invention was initially greater than 33 wt. %, reducing to 20 wt. % after several hours on stream, compared with about a 10 wt. % production of aromatics in the case of the Pt/Re/Al₂O₃ catalyst.

What is claimed is:

1. A catalyst composition which comprises a Group VIII metal species containing low acidity synthetic porous crystalline material characterized by an X-ray diffraction pattern including values substantially as set forth in Table I of the specification and an Alpha Value of not greater than about 150.

2. The catalyst composition of claim 1 wherein the low acidity synthetic porous crystalline material is characterized by an X-ray diffraction pattern including values substantially as set forth in Table II of the specification.

3. The catalyst composition of claim 1 wherein the low acidity synthetic porous crystalline material has a composition comprising the molar relationship

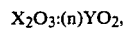

X₂O₃:(n)YO₂, wherein n is at least about 10, X is a trivalent element and Y is a tetravalent element.

4. The catalyst composition of claim 2 wherein the low acidity synthetic porous crystalline material has a composition comprising the molar relationship:

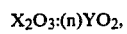

X₂O₃:(n)YO₂, wherein n is at least about 10, X is a trivalent element and Y is a tetravalent element.

5. The catalyst composition of claim 1 wherein the low acidity synthetic porous material possesses equilibrium adsorption capacities of greater than about 4.5 wt. % for cyclohexane vapor and greater than about 10 wt. % for n-hexane vapor.

6. The catalyst composition of claim 3 wherein X is selected from the group consisting of aluminum, boron, iron, gallium and combinations thereof and Y is selected from the group consisting of silicon, germanium and combinations thereof.

7. The catalyst composition of claim 3 wherein X comprises aluminum and Y comprises silicon.

8. The catalyst composition of claim 1 wherein the low acidity synthetic porous crystalline material exhibits an Alpha Value of not greater than about 50.

9. The catalyst composition of claim 1 wherein the low acidity synthetic porous crystalline material exhibits an Alpha Value of not greater than about 10.

10. The catalyst composition of claim 1 wherein the Group VIII metal species is selected from the group consisting of platinum and palladium.

11. The catalyst composition of claim 1 wherein the low acidity synthetic porous crystalline material is further associated with a species of at least one element selected from the group consisting of tin, indium, thallium, lead and sulfur.

12. The catalyst composition of claim 1 wherein the low acidity synthetic crystalline material is combined with a binder comprising the oxide of at least one element selected from the group consisting of Group IVA elements and Group IVB elements.

13. The catalyst composition of claim 1 wherein the low acidity synthetic crystalline material is combined with a binder comprising the oxide of at least one element selected from the group consisting of silicon, germanium, titanium and zirconium.

14. The catalyst composition of claim 13 wherein up to 100 weight percent of the oxide is provided in colloidal form.

15. The catalyst composition of claim 1 wherein said Group VIII metal is present within the range of from about 0.01 to about 5 wt. % of the synthetic porous crystalline material.

16. The catalyst composition of claim 2 wherein said Group VIII metal is present within the range of from about 0.01 to about 5 wt. % of the synthetic porous crystalline material.

17. The catalyst composition of claim 1 wherein said Group VIII metal is present within the range of from about 0.1 to about 2 wt. % of the synthetic porous crystalline material.

18. The catalyst composition of claim 2 wherein said Group VIII metal is present within the range of from about 0.1 to about 2 wt. % of the synthetic porous crystalline material.

19. The catalyst composition of claim 1 wherein said Group VIII metal is present within the range of from about 0.2 to about 1 wt. % of the synthetic porous crystalline material.

20. The catalyst composition of claim 2 wherein said Group VIII metal is present within the range of from about 0.2 to about 1 wt. % of the synthetic porous crystalline material.

* * * * *